US012580041B2

(12) United States Patent
Mackinnon et al.

(10) Patent No.: US 12,580,041 B2
(45) Date of Patent: Mar. 17, 2026

(54) METHOD AND SYSTEM FOR DIFFERENTIAL DRUG DISCOVERY

(71) Applicant: CYCLICA INC., Toronto (CA)

(72) Inventors: Stephen Scott Mackinnon, Burlington (CA); Vijay Shahani, Mississauga (CA); Andreas Windemuth, Belmont, MA (US); Leonard Morayniss, Toronto (CA); Andrew Brereton, Toronto (CA); Naheed Kurji, Toronto (CA)

(73) Assignee: Cyclica Inc., Toronto (CA)

( * ) Notice: Subject to any disclaimer, the term of this patent is extended or adjusted under 35 U.S.C. 154(b) by 496 days.

(21) Appl. No.: 16/765,829

(22) PCT Filed: Nov. 22, 2018

(86) PCT No.: PCT/CA2018/051485
§ 371 (c)(1),
(2) Date: May 21, 2020

(87) PCT Pub. No.: WO2019/100158
PCT Pub. Date: May 31, 2019

(65) Prior Publication Data
US 2020/0357480 A1 Nov. 12, 2020

Related U.S. Application Data

(60) Provisional application No. 62/590,141, filed on Nov. 22, 2017.

(51) Int. Cl.
| | |
|---|---|
| *G16B 15/30* | (2019.01) |
| *G06N 5/02* | (2023.01) |
| *G06N 20/00* | (2019.01) |
| *G16B 5/00* | (2019.01) |
| *G16C 20/10* | (2019.01) |
| *G16C 20/30* | (2019.01) |

(52) U.S. Cl.
CPC .............. *G16B 15/30* (2019.02); *G06N 5/02* (2013.01); *G06N 20/00* (2019.01); *G16B 5/00* (2019.02); *G16C 20/10* (2019.02); *G16C 20/30* (2019.02)

(58) Field of Classification Search
USPC .......................................................... 703/19
See application file for complete search history.

(56) References Cited

U.S. PATENT DOCUMENTS

| | | | |
|---|---|---|---|
| 2005/0170379 A1* | 8/2005 | Kita ...................... | G16B 15/00 |
| | | | 435/6.1 |
| 2012/0265514 A1 | 10/2012 | Hopkins et al. | |
| 2016/0300127 A1 | 10/2016 | Heifets et al. | |
| 2018/0312999 A1* | 11/2018 | Shah ...................... | G16C 20/60 |

FOREIGN PATENT DOCUMENTS

| | | |
|---|---|---|
| CN | 102930152 | 2/2013 |
| CN | 106575320 | 4/2017 |
| CN | 107194203 | 9/2017 |
| JP | 2004-523726 A | 8/2004 |
| JP | 2007-511470 A | 5/2007 |
| JP | 2017-520868 A | 7/2017 |
| WO | 2002/004956 A2 | 1/2002 |
| WO | 2017/113004 A1 | 7/2017 |

OTHER PUBLICATIONS

AbdulHameed, Mohamed Diwan M., et al. "Combined 3D-QSAR modeling and molecular docking study on indolinone derivatives as inhibitors of 3-phosphoinositide-dependent protein kinase-1." Journal of chemical information and modeling 48.9 (2008): 1760-1772. (Year: 2005).*
Oprea, Tudor I., et al. "Computational systems chemical biology." Chemoinformatics and Computational Chemical Biology (2011): 459-488. (Year: 2011).*
Gomes, Joseph, et al. "Atomic convolutional networks for predicting protein-ligand binding affinity." arXiv preprint arXiv:1703. 10603 (2017). (Year: 2017).*
Meyers, J., Brown, N. & Blagg, J. Mapping the 3D structures of small molecule binding sites. J Cheminform 8, 70 (2016). (Year: 2016).*
Tanya Singh, D. Biswas, and B. Jayaram. AADS—An Automated Active Site Identification, Docking, and ScoringProtocol for Protein Targets Based on Physicochemical Descriptors. Journal of Chemical Information and Modeling 2011 51 (10), 2515-2527 (Year: 2011).*
Zhang, Wenjuan, et al. "Polypharmacology in drug discovery: a review from systems pharmacology perspective." Current pharmaceutical design 22.21 (2016): 3171-3181. (Year: 2016).*
International Search Report issued in corresponding application No. PCT/CA2018/051485 mailed Feb. 4, 2019 (4 pages).
Written Opinion of the International Searching Authority issued in corresponding application No. PCT/CA2018/051485 mailed Feb. 4, 2019 (6 pages).
Li, Z. et al., "In Silico Prediction of Drug-Target Interaction networks based on Drug chemical structure and protein sequences"; Scientific Reports, Sep. 11, 2017, vol. 7, No. 11174 (13 pages).

(Continued)

*Primary Examiner* — Olivia M. Wise
*Assistant Examiner* — Jonathan Edward Hayes
(74) *Attorney, Agent, or Firm* — Keller Preece PLLC

(57) ABSTRACT

A method for differential drug discovery involves obtaining a receptor panel which specifies a multitude of targets and a multitude of anti-targets. The method further involves obtaining a small molecule compound (SMC) seed model and derivatizing a first multitude of candidate SMCs from the SMC seed model. For each of the candidate SMCs in the first multitude of candidate SMCs, first desired interactions between the candidate SMC and each of the multitude of targets are simulated, and first undesired interactions between the candidate SMC and each of the multitude of anti-targets are simulated. The method also involves obtaining a first SMC interaction score for each of the candidate SMCs in the first multitude of candidate SMCs based on the first desired interactions and the first undesired interactions, and based on the first SMC interaction score, determining whether at least a minimum score for a drug is reached.

20 Claims, 7 Drawing Sheets

(56) References Cited

OTHER PUBLICATIONS

Recanatini, M. et al., "In Silico Antitarget Screening", Drug Discovery Today: Technologies, Dec. 2004, vol. 1, Issue 3, pp. 209-215 (7 pages).

Molinski, S. V. et al., "Computational Proteome-wide Screening Predicts Neurotoxic Drug-protein Interactome for the Investigational Analgesic BIA 10-2474", Biochem Biophys Res Communications, Jan. 29, 2017, vol. 483, No. 1, pp. 502-508 (7 pages).

Ekins, S. et al., "In Silico Pharmacology for Drug Discovery: Methods for Virtual Ligand Screening and Profiling", British Journal of Pharmacology, Sep. 2007, vol. 152, No. 1, pp. 9-20 (12 pages).

Cyclica, Inc., "Probex Proteome Docking: Identifying Off-Target Interactions", Technical Note, 2016 [online] Retrieved on Jan. 28, 2019 from the Internet: https://cyclicarx.com/s/Ctclica_Validation Note_NonKinome (2 pages).

Supplemental Search Report as received in EP application 18881753.0 dated Jul. 20, 2021.

Xiao Hua Ma et al: "In-Silico Approaches to Multi-target Drug Discovery; Computer Aided Multi-target Drug Design, Multi-target Virtual Screening", Pharmaceutical Research, Kluwer Academic Publishers-Plenum Publishers, NL, vol. 27, No. 5, Mar. 11, 2010 (Mar. 11, 2010), pp. 739-749, XP019793949, ISSN: 1573-904X, DOI: 10.1007/S11095-010-0065-2.

Alexios Koutsoukas et al: "From in silico target prediction to multi-target drug design: Current databases, methods and applications", Journal of Proteomics, Elsevier, Amsterdam, NL, vol. 74, No. 12, May 6, 2011 (May 6, 2011), pp. 2554-2574, XP028108056, ISSN: 1874-3919, DOI: 10.1016/J.JPROT.2011.05.011 [retrieved on May 18, 2011].

Office Action as received in JP application 2020-545828 dated Jan. 31, 2023.

Office Action as received in JP application 2020-545828 dated Nov. 6, 2023.

Zhengwei Li et al., In silico prediction of drug-target interaction networks based on drug chemical structure and protein sequences, Scientific Reports [online], Sep. 11, 2017, vol. 7, pp. 1-13, [Date of retrieval: Jan. 24, 2023], Internet <URL: https://www.nature.com/articles/s41598-017-10724-0>.

CN2018800750470—Office Action and Search Report, dated Dec. 8, 2023.

Communication pursuant to Article 94(3) EPC received in EP Application No. 18881753.0 dated Jul. 2, 2024.

Office Action as received in CA Application No. 3,083,135 dated Nov. 7, 2024.

Second Office Action as received in CN Application No. 2018800750470 dated Sep. 25, 2024.

Final Notice of Reasons for Refusal as received in JP Application No. 2020-545828 dated Aug. 27, 2024.

Examination Report as received in KR Application No. 10-2020-7015513 dated Sep. 24, 2024.

* cited by examiner

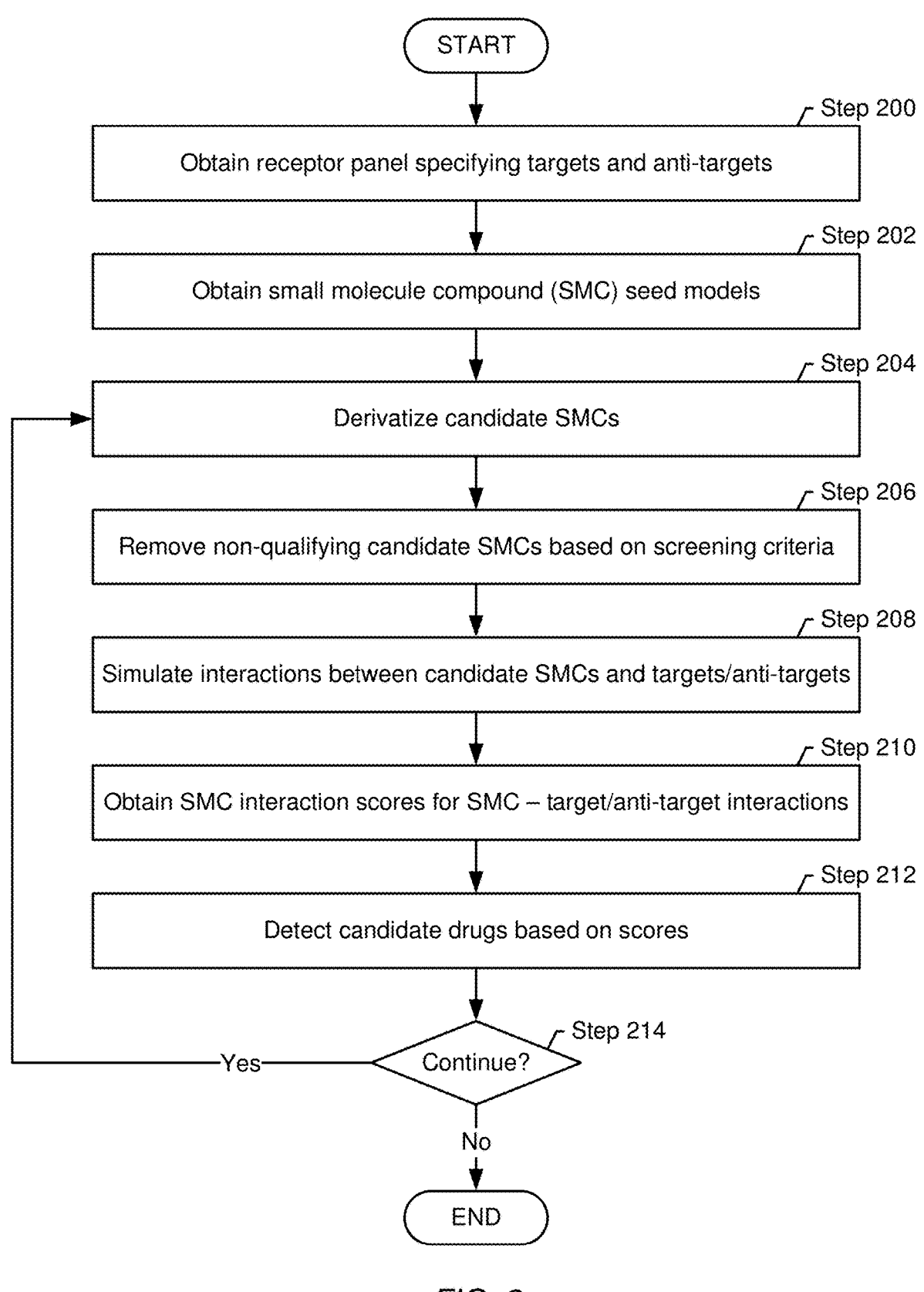
_FIG. 2_

Target List
300

| Protein ID | Protein Classification |
|------------|------------------------|
| O15164 | antitarget |
| P35968 | antitarget |
| P04825 | antitarget |
| P68871 | antitarget |
| P04825 | antitarget |
| Q6PL18 | antitarget |
| Q24645 | antitarget |
| P00099 | antitarget |
| Q04230 | target |
| Q9NAV8 | target |
| P0A387 | target |
| P62775 | target |
| P54512 | target |
| Q00403 | target |
| P0C558 | target |
| P62158 | target |
| P37840 | target |

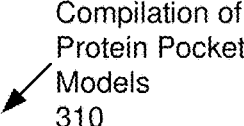

Compilation of
Protein Pocket
Models
310

| Protein ID | Protein 3D Model | Group | Protein Classification | Exemplar Flag |
|---|---|---|---|---|
| Q6PL18 | v0-0-2_pdb_4qsp_0_CHA | 2 | antitarget | FALSE |
| Q6PL18 | v0-0-2_pdb_4qsx_0_CHA | 2 | antitarget | FALSE |
| Q6PL18 | v0-0-2_pdb_4qss_0_CHA | 0 | antitarget | FALSE |
| Q6PL18 | v0-0-2_pdb_4tz8_0_CHA | 2 | antitarget | FALSE |
| Q6PL18 | v0-0-2_pdb_4qst_0_CHA | 1 | antitarget | FALSE |
| Q6PL18 | v0-0-2_pdb_4tyl_0_CHA | 1 | antitarget | TRUE |
| Q6PL18 | v0-0-2_pdb_4tu4_0_CHA | 1 | antitarget | FALSE |
| Q6PL18 | v0-0-2_pdb_5a83_0_CHA | 3 | antitarget | FALSE |
| Q6PL18 | v0-0-2_pdb_5epb_0_CHA | 2 | antitarget | FALSE |
| Q6PL18 | v0-0-2_pdb_5lj0_0_CHA | 3 | antitarget | FALSE |
| Q6PL18 | v0-0-2_pdb_4tz2_0_CHA | 0 | antitarget | FALSE |
| Q6PL18 | v0-0-2_pdb_5f36_0_CHA | 5 | antitarget | FALSE |
| Q6PL18 | v0-0-2_pdb_4qsq_0_CHA | 1 | antitarget | FALSE |
| Q6PL18 | v0-0-2_pdb_5a5o_0_CHA | 4 | antitarget | TRUE |
| Q6PL18 | v0-0-2_pdb_5a5p_0_CHA | 4 | antitarget | FALSE |
| Q6PL18 | v0-0-2_pdb_4qut_0_CHA | 0 | antitarget | FALSE |
| Q6PL18 | v0-0-2_pdb_4tte_0_CHA | 1 | antitarget | FALSE |
| Q6PL18 | v0-0-2_pdb_5a82_0_CHA | 3 | antitarget | TRUE |
| Q6PL18 | v0-0-2_pdb_4qsr_0_CHA | 0 | antitarget | FALSE |
| Q6PL18 | v0-0-2_pdb_5a5q_0_CHA | 4 | antitarget | FALSE |
| Q6PL18 | v0-0-2_pdb_5a81_0_CHA | 3 | antitarget | FALSE |
| Q6PL18 | v0-0-2_pdb_4qsw_0_CHA | 2 | antitarget | TRUE |
| Q6PL18 | v0-0-2_pdb_5f3a_0_CHA | 5 | antitarget | TRUE |
| Q6PL18 | v0-0-2_pdb_5a5n_0_CHA | 0 | antitarget | TRUE |
| Q6PL18 | v0-0-2_pdb_4qsv_0_CHA | 2 | antitarget | FALSE |
| Q6PL18 | v0-0-2_pdb_5a5r_0_CHA | 3 | antitarget | FALSE |

*FIG. 3B*

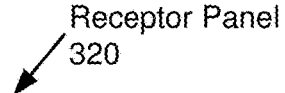

Receptor Panel
320

| Protein ID | Protein 3D Model | Ligand Code | Binding Site | Chain | Protein Classification |
|---|---|---|---|---|---|
| Q6PL18 | v0-0-2_pdb_5a5n_0_CHA | 8WS | 2111 | A | antitarget |
| Q6PL18 | v0-0-2_pdb_4tyl_0_CHA | 39O | 1203 | A | antitarget |
| Q6PL18 | v0-0-2_pdb_4qsw_0_CHA | 38T | 1207 | A | antitarget |
| Q6PL18 | v0-0-2_pdb_5a82_0_CHA | YEJ | 2112 | A | antitarget |
| Q6PL18 | v0-0-2_pdb_5a5o_0_CHA | J5I | 2112 | A | antitarget |
| Q6PL18 | v0-0-2_pdb_5f3a_0_CHA | 5U9 | 1202 | A | antitarget |
| P68871 | v0-0-2_pdb_1j3y_0_CHF | 2FU | 3002 | F | antitarget |
| P68871 | v0-0-2_pdb_1sdl_0_CHD | TMM | 300 | D | antitarget |
| P68871 | v0-0-2_pdb_1j3z_0_CHB | 2FU | 2001 | B | antitarget |
| P68871 | v0-0-2_pdb_1hab_0_CHD | CIN | 300 | D | antitarget |
| P68871 | v0-0-2_pdb_4l7y_0_CHB | IRL | 202 | B | antitarget |
| P68871 | v0-0-2_pdb_1j40_0_CHF | 2FU | 3002 | F | antitarget |
| O15164 | v0-0-2_pdb_5h1t_0_CHC | 7FF | 1103 | C | antitarget |
| O15164 | v0-0-2_pdb_4yat_0_CHB | 4A8 | 1103 | B | antitarget |
| O15164 | v0-0-2_pdb_5h1u_0_CHD | 6KT | 1101 | D | antitarget |
| O15164 | v0-0-2_pdb_4ybm_0_CHB | 4BJ | 1101 | B | antitarget |
| O15164 | v0-0-2_pdb_4ybm_0_CHB | 4BJ | 1102 | B | antitarget |
| O15164 | v0-0-2_pdb_4yad_0_CHB | 4A7 | 1103 | B | antitarget |
| O15164 | v0-0-2_pdb_5h1v_0_CHA | 7FU | 1103 | A | antitarget |
| P35968 | v0-0-2_pdb_3cp9_0_CHB | C19 | 502 | B | antitarget |
| P35968 | v0-0-2_pdb_4asd_0_CHA | BAX | 1500 | A | antitarget |
| P35968 | v0-0-2_pdb_2oh4_0_CHA | PTR | 1052 | A | antitarget |
| P35968 | v0-0-2_pdb_2oh4_0_CHA | PTR | 1057 | A | antitarget |
| P35968 | v0-0-2_pdb_3b8r_0_CHB | 887 | 202 | B | antitarget |
| P35968 | v0-0-2_pdb_4agd_0_CHA | B49 | 2000 | A | antitarget |
| P35968 | v0-0-2_pdb_2qu6_0_CHA | 857 | 501 | A | antitarget |

*FIG. 3C*

METHOD AND SYSTEM FOR DIFFERENTIAL DRUG DISCOVERY

CROSS REFERENCE TO RELATED APPLICATIONS

The present application claims priority under 35 U.S.C. § 119(e) to U.S. Provisional Application No. 62/590,141, filed on Nov. 22, 2017, having at least one of the same inventors as the present application, and entitled, "METHOD AND SYSTEM FOR DIFFERENTIAL DRUG DISCOVERY". U.S. Provisional Application No. 62/590,141 is incorporated herein by reference.

BACKGROUND

Many diseases have complex biological pathologies involving several pathways. Small molecule drugs are traditionally designed for single protein targets, but have multiple off-target protein interactions (i.e., polypharmacology). The average small molecule compound (SMC) is believed to bind 30-300 different proteins within a living organism. Normally, a drug molecule is intended to bind only one of them, the target. The others are unintended off-target interactions which may be beneficial or adverse, and can occur in homologous or non-homologous proteins. In the field of multi-targeted drug design, one small molecule drug that targets multiple proteins could improve therapies for complex pathologies. However, due to various complications, it has been difficult to design small molecule drugs that can bind multiple targets simultaneously.

SUMMARY

In general, one or more embodiments relate to a method for differential drug discovery, the method comprising: obtaining a receptor panel, wherein the receptor panel specifies a plurality of targets and a plurality of anti-targets; obtaining a small molecule compound (SMC) seed model; derivatizing a first plurality of candidate SMCs from the SMC seed model; for each of the candidate SMCs in the first plurality of candidate SMCs, simulating first desired interactions between the candidate SMC and each of the plurality of targets; for each of the candidate SMCs in the first plurality of candidate SMCs, simulating first undesired interactions between the candidate SMC and each of the plurality of anti-targets; obtaining a first SMC interaction score for each of the candidate SMCs in the first plurality of candidate SMCs based on the first desired interactions and based on the first undesired interactions; and based on the first SMC interaction score, determining whether at least a minimum score for a drug is reached.

In general, one or more embodiments relate to a system for differential drug discovery, the system comprising: a derivatization engine configured to derivatize a plurality of candidate SMCs from a small molecule compound (SMC) seed model; a molecular docking simulation engine configured to: for each of the candidate SMCs in the plurality of candidate SMCs, simulate desired interactions between the candidate SMC and each of a plurality of targets specified in a receptor panel; for each of the candidate SMCs in the plurality of candidate SMCs, simulate undesired interactions between the candidate SMC and each of a plurality of anti-targets specified in the receptor panel; a scoring engine configured to: obtain an SMC interaction score for each of the candidate SMCs in the plurality of candidate SMCs based on the desired interactions and based on the undesired interactions; and based on the first SMC interaction score, determine whether at least a minimum score for a drug is reached.

In general, one or more embodiments relate to non-transitory computer readable medium comprising computer readable program code for differential drug discovery, the computer readable program code causing a computer system to: obtain a receptor panel, wherein the receptor panel specifies a plurality of targets and a plurality of anti-targets; obtain a small molecule compound (SMC) seed model; derivatize a first plurality of candidate SMCs from the SMC seed model; for each of the candidate SMCs in the first plurality of candidate SMCs, simulate first desired interactions between the candidate SMC and each of the plurality of targets; for each of the candidate SMCs in the first plurality of candidate SMCs, simulate first undesired interactions between the candidate SMC and each of the plurality of anti-targets; obtain a first SMC interaction score for each of the candidate SMCs in the first plurality of candidate SMCs based on the first desired interactions and based on the first undesired interactions; and based on the first SMC interaction score, determine whether at least a minimum score for a drug is reached.

Other aspects of the embodiments will be apparent from the following description and the appended claims.

BRIEF DESCRIPTION OF DRAWINGS

The present embodiments are illustrated by way of example and are not intended to be limited by the figures of the accompanying drawings.

FIG. 2 shows a flowchart, in accordance with one or more embodiments.

FIG. 3B shows a compilation of protein pocket models, in accordance with one or more embodiments.

FIG. 3C shows an example of a receptor panel, in accordance with one or more embodiments.

DETAILED DESCRIPTION

Figure 1:
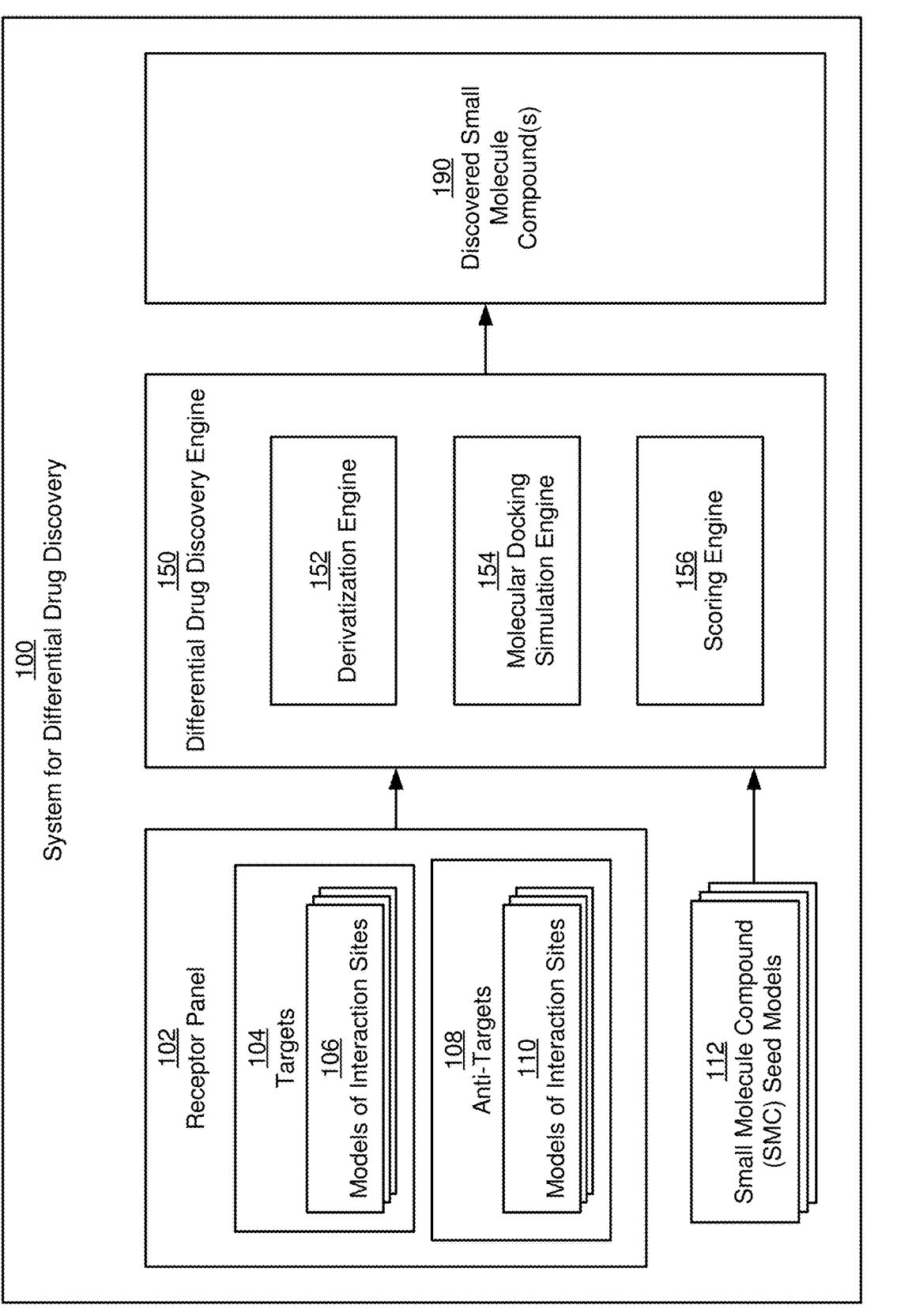
FIG. 1 shows a block diagram of a system in accordance with one or more embodiments.

Specific embodiments disclosed herein will now be described in detail with reference to the accompanying figures. Like elements in the various figures may be denoted by like reference numerals and/or like names for consistency.

The following detailed description is merely exemplary in nature, and is not intended to limit the embodiments disclosed herein or the application and uses of embodiments disclosed herein. Furthermore, there is no intention to be bound by any expressed or implied theory presented in the preceding technical field, background, brief summary or the following detailed description.

In the following detailed description of some embodiments disclosed herein, numerous specific details are set forth in order to provide a more thorough understanding of the various embodiments disclosed herein. However, it will be apparent to one of ordinary skill in the art that the embodiments may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

A polypharmacological drug that interacts with multiple targets (e.g. proteins) may be particularly valuable because many diseases are known to involve numerous proteins. Accordingly, a drug capable of targeting multiple proteins associated with the disease may be more potent than a drug that is specific to one protein only.

However, finding a small molecule compound (SMC) that interacts with multiple targets may be challenging for various reasons. Specifically, for example, the pockets (or more generally speaking: the interaction sites) of the target proteins may have different geometries and/or physicochemical configurations. Further, the structure of SMCs tends to be dynamic, e.g., many conformations of the same SMC may exist. Accordingly, predicting SMC-target compatibility may be a non-trivial task. Specifically, while similar pockets are more likely to bind a common SMC, pocket similarity is not strictly required for compatibility. Instead, due to conformational changes, an SMC may be able to interface with very different pockets.

In one or more embodiments, a multi-targeted drug design (MTDD) strategy is used to identify small molecule compounds (SMCs) with desired characteristics. The MTDD strategy as subsequently discussed may identify pharmaceutical therapies that simultaneously target multiple targets. The MTDD strategy may, thus, result in the identification of promiscuous drugs that affect a disease network rather than a single target.

More specifically, the method and system according to one or more embodiments exploit combinatorics to mitigate the risk of target incompatibility. That is, according to one or more embodiments, an SMC is not designed for any one specific target. Instead, a receptor panel, which may include several of both targets and anti-targets, is employed. In this way, the MTDD strategy of one or more embodiments increases the likelihood of finding an SMC capable of interacting with at least one or some of the targets on the receptor panel, while avoiding interaction with the anti-targets. MTDD strategies in accordance with one or more embodiments may thus be used to develop a single drug with multiple affinities or a combination of drugs to be used as a combinatorial treatment.

The MTDD strategy may be based on a de novo design of SMCs using computational methods, in which candidate drugs are simulatively designed from building blocks such as molecular fragments, atoms, etc.

Turning to FIG. 1, a system (100) for differential drug discovery, in accordance with one or more embodiments, is shown. The system (100) comprises a differential drug discovery engine (150). Inputs to the differential drug discovery engine (150) include a receptor panel (102) and small molecule compound (SMC) seed models (104). The output produced by the differential drug discovery engine (150)

includes one or more discovered SMCs (190). More specifically, the output includes one or more models (formulas, descriptions) of the discovered SMCs. Each of these components is subsequently described.

The receptor panel (112), in accordance with one or more embodiments, may specify targets (104) and anti-targets (108). A target (104) may be any cellular component in cells of any living species, to be modulated by an SMC. A target may be a macromolecule, e.g., a protein. When treating a medical condition, the modulation of the target by a drug (an SMC) may produce a beneficial result. In contrast, anti-targets (108) may be macromolecules with which the drug to be developed is not supposed to interact. Modulation of anti-targets may, for example, produce no known effect or undesirable or counter-productive pharmacologies, such as toxicities. With the receptor panel (112) specifying targets (104) with which an SMC is supposed to interact and anti-targets (108) with which the SMC is not supposed to interact, thus, establishes fitness objectives for the SMC to be developed, based on these desired and undesired interactions. The receptor panel (112) may be established based on a certain objective, such as the treatment or a curing of a disease or, more generally, based on the objective to affect an organism in a desired manner. Based on this objective, a receptor panel (102) may be constructed based on the targets (104) and anti-targets (108). The construction of a receptor panel is discussed in the flowchart of FIG. 2, and an example is provided in FIGS. 3A, 3B, and 3C.

A target may have multiple interaction sites that allow interaction of a drug with the target. Each of these interaction sites may be represented in the receptor panel (102) by one or more models of interaction sites (106). Many models of interaction sites, e.g., hundreds or even thousands of models of interaction sites, may be included in the receptor panel (102). Those skilled in the art will appreciate that an interaction site may be any kind of a structure or region (e.g., a binding site such as a pocket) of a protein that allows interaction with the protein. Further, interactions between an SMC and a protein are not limited to ligand-pocket-binding interactions between the SMC and the protein. Instead, any kind of interaction between the SMC and the protein are within the scope of the invention. Multiple models of an interaction site may be in the receptor panel to accommodate multiple conformations. As a result, the receptor panel (102) may be based on any number of targets (104), each of which may have any number of interaction sites that may be included as models of interaction sites (106) in the receptor panel (102). Further, even a single interaction site may be modeled using multiple models, to represent different conformational configurations. Some or all of the known models may be included.

The existence of multiple targets (104) provided as models of interaction sites (106), in accordance with one or more embodiments, is assumed to increase the likeliness of discovering an SMC that interacts with at least some of the interaction sites. For example, identifying an SMC that interacts with three out of ten targets is likely to be less challenging than identifying an SMC that interacts with three out of three targets. Embodiments of the invention, thus, benefit from combinatorics. The combinatorial approach may be particularly beneficial in view of the known difficulties associated with systematically predicting the likeliness of interaction based on known interactions between SMCs and proteins. In case of ligand-pocket bindings, geometric characteristics (pocket volume, surface area, mouth size, etc.) of the pocket matter. However, due to the numerous possible molecular conformations, a first ligand that binds well with a pocket does not necessarily suggest that a second ligand with a very different geometry does not bind with the same pocket. Similarly, while a first ligand may bind well with a pocket, a second ligand that is only slightly different from the first ligand may not bind well with the same pocket. In view of this potentially poor predictability, the availability of numerous targets with the potential to interact with an SMC increases the likeliness of discovering an SMC with acceptable performance characteristics.

Continuing with the discussion of receptor panel (102), anti-targets (108) may be specified in the same manner. However, the models of the interaction sites (110) for anti-targets are based on those proteins that were previously identified as not to be targeted by the SMC to be developed.

In one or more embodiments, priority weights may be assigned to the targets (104) and anti-targets (108). These weights may indicate the importance of interaction with the respective targets (104) and the importance of avoiding interaction with the respective anti-targets (108).

Figure 3A:
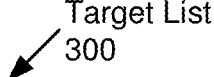
FIG. 3A shows an example of a target list, in accordance with one or more embodiments.

Further, a detailed description of how a receptor panel may be established is provided in Step 200 of FIG. 2, and an example is provided in FIGS. 3A-3C.

The SMC seed models (112), in accordance with one or more embodiments, are candidate models of SMCs for which the method of FIG. 2 is to be performed to ultimately discover one or more SMCs with desired characteristics, based on the receptor panel (102). As discussed in FIG. 2, the SMC seed models (112) may be initially tested for the desired characteristics, and may then be incrementally modified until the desired characteristics are discovered. One or more seed models (112) may be provided, and the provided seed model(s) may be based on one or more criteria: The provided seed model(s) may be selected based on prior knowledge. For example, a seed model may be selected based on knowledge that it does interact with one or more of the interaction sites of the targets specified in the receptor panel. A seed model may further be derivatized from a preselected scaffold. A seed model may also be selected to avoid interaction with anti-targets. A seed model may represent a known SMC such as an existing drug and may be represented by a SMILES string. For example, the drug Aspirin may be represented by the SMILES string "CC(=O)OC1=CC=CC=C1C(=O)O" when used as an SMC seed model.

Continuing with the discussion of the system (100), the differential drug discovery engine (150), in accordance with one or more embodiments, accepts the receptor panel (102) and the SMC seed model(s) (112) as inputs to eventually provide a discovered SMC (190) as an output. The methods performed by the differential drug discovery engine (150), in accordance with one or more embodiments, aim for obtaining a discovered SMC (190) that interacts with multiple targets (106) while avoiding interaction with anti-targets by leveraging the combinatorics resulting from a large number of targets (104) in the receptor panel (102). The differential drug discovery engine (150) may include a derivatization engine (152), a molecular docking simulation engine (154) and a scoring engine (156).

The derivatization engine (152) includes a set of machine-readable instructions configured to derivatize candidate SMCs from either the seed models in a first iteration, or from previously analyzed candidate SMCs in subsequent iterations. The derivatization of candidate SMCs is described below in Steps 204 and 206 of FIG. 2.

The molecular docking simulation engine (154) includes a set of machine-readable instructions configured to simulate interactions between candidate SMCs and the targets and anti-targets specified in the receptor panel. The simulation is described below in Step 208 of FIG. 2.

The scoring engine (156) includes a set of machine-readable instructions configured to score the simulated interactions of Step 208 to obtain a single score for each candidate SMC. The simulation is described below in Step 210 of FIG. 2.

In combination, the derivatization engine (152), the molecular docking simulation engine (154), and the scoring engine (156), iteratively produce candidate SMCs that may eventually qualify as a a discovered SMC (190) with the desired characteristics. A discussion of the iterative execution is provided below with reference to FIG. 2.

FIG. 2 shows a flowchart in accordance with one or more embodiments. While the various steps in this flowchart are provided and described sequentially, one of ordinary skill will appreciate that some or all of the steps may be executed in different orders, may be combined or omitted, and some or all of the steps may be executed in parallel. Furthermore, the steps may be performed actively or passively. For example, some steps may be performed using polling or be interrupt driven in accordance with one or more embodiments. By way of an example, determination steps may not require a processor to process an instruction unless an interrupt is received to signify that condition exists in accordance with one or more embodiments. As another example, determination steps may be performed by performing a test, such as checking a data value to test whether the value is consistent with the tested condition in accordance with one or more embodiments.

The flowchart of FIG. 2 shows a method for differential drug discovery, in accordance with one or more embodiments. The method for differential drug discovery is based on a fragment growth strategy (FGS) to computationally optimize an SMC using the target interaction sites of 3D protein structures as specified in the receptor panel. FGS may include at least the steps of: finding lead scaffolds that 'fit' a pocket using docking, molecular dynamics (MD) simulations, or machine learning approaches based on featurized SMCs and/or featurized interaction sites; modifying the SMCs, rescoring, and selecting best new SMCs; and iterating to optimize the results, as subsequently discussed. With every iteration, changes are made to the SMC(s), either by redesigning some of the SMC fragments, re-derivatizing some of the molecule, building onto the molecule, or removing from the molecule.

In one or more embodiments, the subsequently described method optimizes the SMC(s) against an entire receptor panel of several targets and anti-targets. In an example where the receptor panel includes 64 different targets, 36 of the 64 targets may include targets that may have a positive value therapeutically, and the remaining 28 targets may include anti-targets that should be optimized against. Using the disclosed method, a given SMC of this example may be evaluated against all 64 different targets of the receptor panel to determine predicted interactions, and to create a polypharmacology score. The polypharmacology score may be computed such that it rewards predicted interactions with multiple targets, and penalizes interactions with the anti-targets.

Turning to the flowchart, in Step 200, the receptor panel is obtained. The receptor panel may be obtained in its final format, as illustrated in the example of FIG. 3C, or alternatively the receptor panel may be constructed. Constructing the receptor panel may be performed as follows. First, a selection of proteins (or other targets), including targets and anti-targets may be obtained, e.g., as a list of proteins, as shown in the example of FIG. 3A. The provided selection of proteins may be established based on a desired therapeutic effect, for example, when treating a disease. Next, the receptor panel may be compiled by mapping the 3D structures (e.g., the list of atoms that compose the protein with their 3D locations) for each of the proteins on the list. Each of these 3D locations may be an interaction site such as a pocket. Further, for each of the mapped 3D locations, known configurations (as a result of conformational changes) may be obtained. An example (limited to a single protein) is provided in FIG. 3B. Subsequently, a clustering may be performed to reduce the total number of 3D locations. The clustering may be performed using any measure of similarity between 3D structures. An exemplar may be selected for each of the clusters, and the receptor panel is obtained by compiling the exemplars for targets and anti-targets. An example for a receptor panel is shown in FIG. 3C.

In Step 202, the SMC seed model(s) is/are obtained. As previously described, an SMC seed model may be obtained as a SMILES representation.

In Step 204, candidate SMCs are derivatized. Step 204 may be skipped for the first execution cycle of the method of FIG. 2, i.e., the steps following Step 204 may directly operate on the SMC seed model(s). For subsequent execution cycles, the derivatization is performed in accordance with one or more embodiments, as subsequently described.

With each execution of Step 204, the SMCs under consideration may be computationally modified by substituting functional groups with other chemical fragments. Thus, new SMCs are obtained from the parent SMCs, i.e., SMCs obtained from a previous execution cycle or SMC seed models may be modified. More specifically, an SMC may be modified by breaking the SMC into fragments and by exchanging, adding, and/or removing fragments from the SMC. These operations may be governed by sets or rules to ensure that major structural features are preserved. The set of rules may be based on, for example, the retrosynthetic combinatorial procedure (RECAP) or the breaking retrosynthetically interesting chemical substructures (BRICS). Those skilled in the art will recognize that the invention is not limited to particular sets of rules to establish how SMCs are computationally modified. Any method capable of chemically meaningfully modifying SMCs may be used. Further, the modification may be of any size, ranging from modifications of single atoms to modifications of larger chemical substructures. In one embodiment, the fragmenting is performed exhaustively. Consider, for example a molecule A-B-C. An exhaustive fragmentation may produce the fragments A-B, B-C, A, B, and C. The obtained fragments may then be modified by the addition of one or more other fragments obtained from a fragment library to obtain the new candidate SMCs. While the derivatization of candidate SMCs may be performed randomly, certain limitations may be imposed when modifying the SMCs. For example, a minimum similarity to the parent SMCs may be required, a portion of the parent SMC may be required to be kept intact, etc.

The derivatization of Step 204 may be performed on all SMCs obtained from the previous execution cycle, or on a subset of the SMCs. For example, only the top SMCs, based on an SMC interaction score, may be considered. Selection criteria may change between early (exploratory) and late (refinement) stages of the optimization.

In Step 206, non-qualifying candidate SMCs are removed from the candidate SMCs based on screening criteria. Screening criteria may include, but are not limited to requiring candidate SMCs to have a minimum similarity to known drugs, requiring the SMCs to be synthesizable using no more than a specified effort, requiring certain ADMET characteristics, and/or requiring other desirable computed properties such as optimal lipophilicity or the absence of unstable chemical groups, etc. Selection criteria may change between early (exploratory) and late (refinement) stages of the optimization.

Further, in one or more embodiments, a clustering algorithm may be used to identify representative SMCs from the set of candidate SMCs with similar polypharmacological profiles to undergo subsequent rounds of optimization.

In Step 208, interactions of the SMCs with targets and anti-targets in the receptor panel are simulated, in accordance with one or more embodiments. As previously noted, an interaction may be a docking of the SMC to a pocket, or more generally, any kind of interaction of the SMC with an interaction site. The simulation may be performed for all combinations of an SMC and an interaction site of the targets and anti-targets. Each of these interactions may be scored to assess the degree of interaction. The simulation may be performed in various ways, as subsequently described. After completion of Step 208, the interactions of each of the SMCs with each of the interaction sites (targets and anti-targets) in the target panel may be assessed based on the obtained scores.

In one embodiment, a molecular docking approach is used to simulate interactions between SMCs and targets (and anti-targets). The molecular docking approach may rely on Monte Carlo simulations to minimize an energy associated with an interaction between the SMC and the interaction site. An energy-based score may be obtained based on the pose of the SMC resulting in an interaction.

In one embodiment, a molecular dynamics approach is used to simulate interactions between SMCs and targets (and anti-targets). A physics engine operating on an SMC and an interaction site may determine whether binding, or more generally, interaction, occurs. Once interaction is detected, an energy-based score may be obtained for the configuration of the SMC and the interaction site.

In one embodiment, a machine learning approach is used to simulate interactions between SMCs and targets (and anti-targets) based on featurized SMCs and featurized targets/anti-targets. The machine learning approach may use a predictive algorithm such as a random forest, a convolutional neural network or any other predictive algorithm capable of making a quantitative prediction. The prediction may be a binding affinity. The predictive algorithm may have been previously trained using historical data, where interactions (or lack of interactions) between SMCs and interaction sites are known. The trained predictive algorithm may, thus, predict a binding affinity indicating to what degree an SMC under consideration would interact with an interaction site under consideration. The predicted affinity may serve as a score.

After completion of Step 208, a score is available for each of the interactions between the SMCs under consideration and the interaction sites under consideration.

Figure 4:
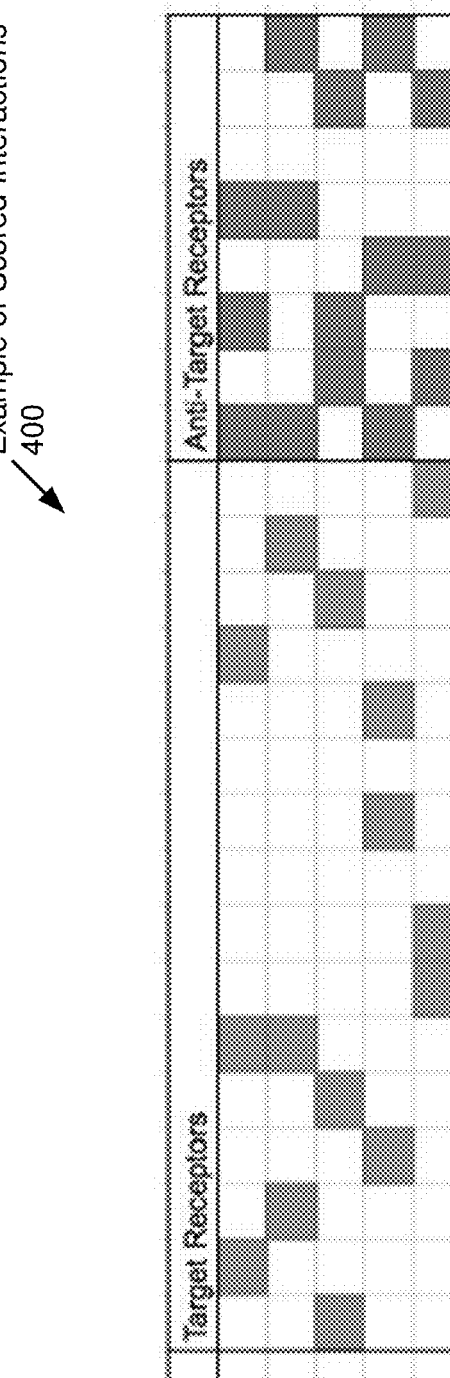
FIG. 4 shows an example of scored interactions, in accordance with one or more embodiments.

In Step 210, SMC interaction scores are obtained for SMC—target/anti-target interactions through evaluation of the scores obtained in Step 208. Specifically, one SMC interaction score is obtained for each of the SMCs. The SMC interaction score may indicate to what degree an SMC interacts with the targets in the receptor panel while avoiding interaction with the anti-targets in the receptor panel. Broadly speaking, an SMC interaction score may reward predicted interactions with targets in the receptor panel (resulting in an increase of the SMC interaction score) while punishing interaction with anti-targets in the receptor panel (resulting in a decrease of the SMC interaction score). The SMC interaction scores may be computed in various ways. For example, the weighted sum of an SMC's top three (or five) target interaction scores minus (−) the top three (or five) anti-target interaction scores may be used. An example for using the top three interaction scores is shown in FIG. 4, described below. Further, in one or more embodiments, SMC interaction scores may be designed to reward receptor combinations from the same or different biological pathways, which are believed to provide synergistic therapeutic outcomes. Different weights may also be applied to different interaction sites, to emphasize/de-emphasize the contribution of these interaction sites to the SMC interaction score. For example, a weight of 1.5 may be assigned to primary interaction sites, a weight of 1.0 may be assigned to secondary interaction sites, and a weight of 0.5 may be assigned to minor interaction sites, to encourage exploration among the more important interaction sites or targets. Based on the SMC interaction scores, the associated candidate SMCs may be ranked.

In Step 212, the SMC interaction scores are assessed to determine whether one or more of the candidate SMCs qualify as a drug. An SMC may qualify as a drug if the associated SMC interaction score reaches or exceeds a minimum score. Other criteria that can be computed for an SMC may also be used to qualify an SMC as a drug, for example, molecular weight, solubility, and/or other relevant properties.

Step 214 is used to determine whether another iteration should be performed, or whether the execution of the method should be terminated. The determination may be made based on whether at least one of the SMCs qualify as a drug. The determination may be made based on convergence. Convergence may be assessed based on the scores obtained in Step 208. Convergence may be detected once the scores have reached a certain threshold, have plateaued (e.g., with no significant improvements after two iterations), etc. Additionally or alternatively, cost may be the determining factor. Cost may be measured using CPU time spent on performing the method of FIG. 2, and the simulation may be terminated after a certain amount of CPU time has been spent. If another iteration is to be performed, the execution of the method may proceed with Step 204. Alternatively, the execution of the method may terminate.

The steps of FIG. 2 may be performed for many candidate SMCs. For example, 10 s, 100 s, 1000 s, or 10000 s of candidate SMCs may be processed. These candidate SMCs may originate from a single or multiple SMC seed models.

Turning to FIGS. 3A, 3B, and 3C, examples for generating a receptor panel, in accordance with one or more embodiments, are provided. In FIG. 3A, a target list (300) is shown. The target list (300) enumerates proteins. The proteins may have been selected based on a desired therapeutic effect, for example, when treating a disease. Each of the proteins, in the example, is identified by a UniProt ID. Further, a protein classification is associated with each protein. The classification indicates whether the protein is intended to serve as a target or as an anti-target.

FIG. 3B shows a compilation of protein pocket models (310), in accordance with one or more embodiments. In the example of FIG. 3B, only protein pocket models for the protein "Q6PL18" are shown. While not shown in FIG. 3B, protein pocket models for all proteins enumerated in the target list (300) in FIG. 3A are obtained when executing Step 200 of FIG. 2.

FIG. 3C shows an example of a receptor panel (320), in accordance with one or more embodiments. The receptor panel (320), for each of the proteins enumerated in the target list (300) in FIG. 3A, includes a set of representative protein pocket models, obtained from the compilation of protein pocket models (310) in FIG. 3B.

FIG. 4 shows an example of scored interactions (400), in accordance with one or more embodiments. In FIG. 4, results for five SMCs (C001-C005) and 16 targets and eight anti-targets are shown. The top three targets, based on the SMC interaction scores obtained in Step 210, are marked, and further the top three anti-target interaction scores are also marked. As FIG. 4 illustrates, each SMC may have different sets of favorable targets and anti-targets, according to one or more embodiments.

Various embodiments have one or more of the following advantages. Embodiments of the disclosure leverage combinatorics. Due to the use of relatively large receptor panels that may further include multiple models of the same protein, the likeliness of identifying an SMC that successfully interacts with at least some of the targets increases. A larger number of targets in a receptor panel may further have the additional benefit of allowing the normalization of interaction scores, where the scores of ligands that are high or low across all targets may be adjusted down or up, respectively, to avoid selecting promiscuous ligands, i.e., those that are generally more sticky towards all targets. Also, the use of anti-targets provides additional compounds for normalization and allows for an optimization against target interactions that may be problematic for the specific condition or the SMC scaffold.

Pairing the receptor panel with an iterative optimization strategy may permit simultaneous exploration across chemical space and receptor panel target space. Each SMC may have its own distinct set of targets. In the following generation, the SMC's derivatives could improve relative to the same targets, or identify a new combination of targets.

Embodiments may require only three-dimensional (3D) structures of the targets and anti-targets and one or more seed structures. Because 3D structure-based molecular docking simulations are used, molecular flexibility in the ligand and receptor allow for the detection of compatible target pairs that have dissimilar binding site geometries. No experimental target SMC binding data are required. The method and system of one or more embodiments are computational. That is, the disclosed methods may be executed entirely in silico. However, in vitro experimentation may be integrated as well, without departing from the invention.

In therapeutic applications, a polypharmacological drug, obtained using the described methods, may be used to treat a disease by regulating multiple targets. The polypharmacological drug may be more potent than a single conventional drug, and the risk of loss of efficacy due to single-target mutations may be greatly reduced. Another significant advantage of using a single polypharmacological drug rather than a cocktail of individual drugs may be that the risk of drug-drug interactions is reduced.

Figure 5A:
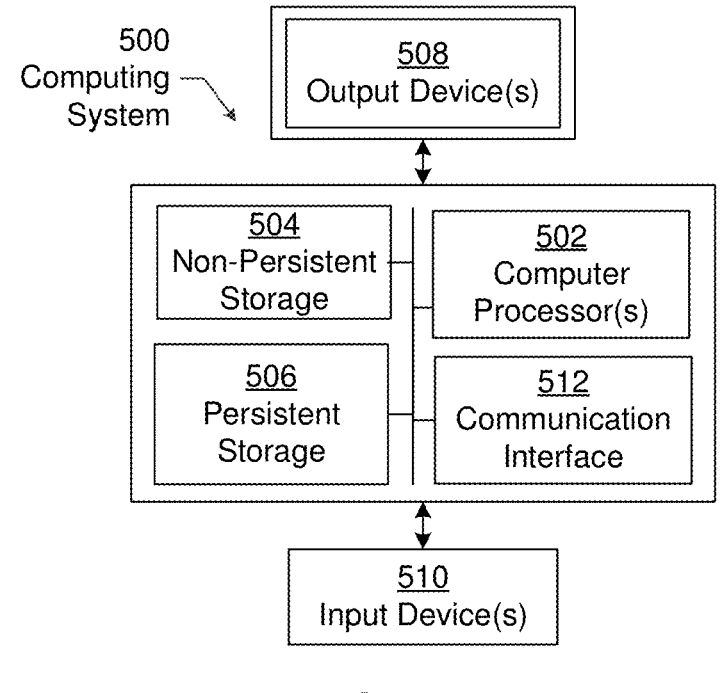
FIG. 5A and FIG. 5B show a computing system, in accordance with one or more embodiments.

Embodiments of the disclosure may be implemented on a computing system. Any combination of mobile, desktop, server, router, switch, embedded device, or other types of hardware may be used. For example, as shown in FIG. 5A, the computing system (500) may include one or more computer processors (502), non-persistent storage (504) (e.g., volatile memory, such as random access memory (RAM), cache memory), persistent storage (506) (e.g., a hard disk, an optical drive such as a compact disk (CD) drive or digital versatile disk (DVD) drive, a flash memory, etc.), a communication interface (512) (e.g., Bluetooth interface, infrared interface, network interface, optical interface, etc.), and numerous other elements and functionalities.

The computer processor(s) (502) may be an integrated circuit for processing instructions. For example, the computer processor(s) may be one or more cores or micro-cores of a processor. The computing system (500) may also include one or more input devices (510), such as a touchscreen, keyboard, mouse, microphone, touchpad, electronic pen, or any other type of input device.

The communication interface (512) may include an integrated circuit for connecting the computing system (500) to a network (not shown) (e.g., a local area network (LAN), a wide area network (WAN) such as the Internet, mobile network, or any other type of network) and/or to another device, such as another computing device.

Further, the computing system (500) may include one or more output devices (508), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (502), non-persistent storage (504), and persistent storage (506). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

Figure 5B:
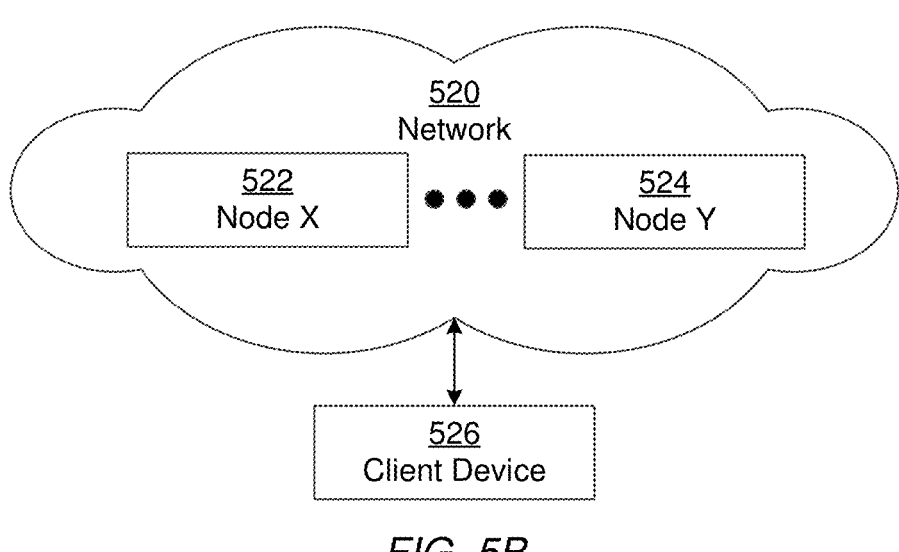

The computing system (500) in FIG. 5A may be connected to or be a part of a network. For example, as shown in FIG. 5B, the network (520) may include multiple nodes (e.g., node X (522), node Y (524)). Each node may correspond to a computing system, such as the computing system shown in FIG. 5A, or a group of nodes combined may correspond to the computing system shown in FIG. 5A. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system (500) may be located at a remote location and connected to the other elements over a network.

Although not shown in FIG. 5B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (522), node Y (524)) in the network (520) may be configured to provide services for a client device (526). For example, the nodes may be part of a cloud computing system. The nodes may include functionality to receive requests from the client device (526) and transmit responses to the client device (526). The client device (526) may be a computing system, such as the computing system shown in FIG. 5A. Further, the client device (526) may include and/or perform all or a portion of one or more embodiments of the disclosure.

The computing system or group of computing systems described in FIGS. 5A and 5B may include functionality to perform a variety of operations disclosed herein. For example, the computing system(s) may perform communication between processes on the same or different system. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name and/or address associated with the first socket object. The client process then transmits the connection request to the server process. Depending on availability, the server process may accept the connection request, establishing a communication channel with the client process, or the server process, busy in handling other operations, may queue the connection request in a buffer until server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, only one authorized process may mount the shareable segment, other than the initializing process, at any given time.

Other techniques may be used to share data, such as the various data described in the present application, between processes without departing from the scope of the disclosure. The processes may be part of the same or different application and may execute on the same or different computing system.

Rather than or in addition to sharing data between processes, the computing system performing one or more embodiments of the disclosure may include functionality to receive data from a user. For example, in one or more embodiments, a user may submit data via a graphical user interface (GUI) on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered by the web client and displayed on the user device.

Once data is obtained, such as by using techniques described above or from storage, the computing system, in performing one or more embodiments of the disclosure, may extract one or more data items from the obtained data. For example, the extraction may be performed as follows by the computing system in FIG. 5A. First, the organizing pattern (e.g., grammar, schema, layout) of the data is determined, which may be based on one or more of the following: position (e.g., bit or column position, Nth token in a data stream, etc.), attribute (where the attribute is associated with one or more values), or a hierarchical/tree structure (consisting of layers of nodes at different levels of detail-such as in nested packet headers or nested document sections). Then, the raw, unprocessed stream of data symbols is parsed, in the context of the organizing pattern, into a stream (or layered structure) of tokens (where each token may have an associated token "type").

Next, extraction criteria are used to extract one or more data items from the token stream or structure, where the extraction criteria are processed according to the organizing pattern to extract one or more tokens (or nodes from a layered structure). For position-based data, the token(s) at the position(s) identified by the extraction criteria are extracted. For attribute/value-based data, the token(s) and/or node(s) associated with the attribute(s) satisfying the extraction criteria are extracted. For hierarchical/layered data, the token(s) associated with the node(s) matching the extraction criteria are extracted. The extraction criteria may be as simple as an identifier string or may be a query provided to a structured data repository (where the data repository may be organized according to a database schema or data format, such as XML).

The extracted data may be used for further processing by the computing system. For example, the computing system of FIG. 5A, while performing one or more embodiments of the disclosure, may perform data comparison. Data comparison may be used to compare two or more data values (e.g., A, B). For example, one or more embodiments may determine whether A>B, A=B, A!=B, A<B, etc. The comparison may be performed by submitting A, B, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if A>B, B may be subtracted from A (i.e., A−B), and the status flags may be read to determine if the result is positive (i.e., if A>B, then A−B>0). In one or more embodiments, B may be considered a threshold, and A is deemed to satisfy the threshold if A=B or if A>B, as determined using the ALU. In one or more embodiments of the disclosure, A and B may be vectors, and comparing A with B requires comparing the first element of vector A with the first element of vector B, the second element of vector A with the second element of vector B, etc. In one or more embodiments, if A and B are strings, the binary values of the strings may be compared.

The computing system in FIG. 5A may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 5A may include functionality to provide raw and/or processed data, such as results of comparisons and other processing. For example, providing data may be accomplished through various presenting methods. Specifically, data may be provided through a user interface provided by a computing device. The user interface may include a GUI that displays information on a display device, such as a computer monitor or a touchscreen on a handheld computer device. The GUI may include various GUI widgets that organize what data is shown as well as how data is provided to a user. Furthermore, the GUI may provide data directly to the user, e.g., data provided as actual data values through text, or rendered by the computing device into a visual representation of the data, such as through visualizing a data model.

For example, a GUI may first obtain a notification from a software application requesting that a particular data object be provided within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Data may also be provided through various audio methods. In particular, data may be rendered into an audio format and provided as sound through one or more speakers operably connected to a computing device.

Data may also be provided to a user through haptic methods. For example, haptic methods may include vibrations or other physical signals generated by the computing system. For example, data may be provided to a user using a vibration generated by a handheld computer device with a predefined duration and intensity of the vibration to communicate the data.

The above description of functions presents only a few examples of functions performed by the computing system of FIG. 5A and the nodes and/or client device in FIG. 5B. Other functions may be performed using one or more embodiments of the disclosure.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

The embodiments and examples set forth herein were presented in order to best explain the present invention and its particular application and to thereby enable those skilled in the art to make and use the invention. However, those skilled in the art will recognize that the foregoing description and examples have been presented for the purposes of illustration and example only. The description as set forth is not intended to be exhaustive or to limit the invention to the precise form disclosed.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

16

What is claimed is:

1. A method for differential drug discovery, the method comprising:

generating a digital protein receptor panel relating to a pharmaceutical therapy of a first protein target, a second protein target, a first protein anti-target, and a second protein anti-target by:

generating, for the first protein target, a first set of interaction sites comprising a first set of three-dimensional (3D) protein structure models to accommodate molecular conformations;

generating, for the second protein target, a second set of interaction sites comprising a second set of 3D protein structure models to accommodate molecular conformations;

generating, for the first protein anti-target, a third set of interaction sites comprising a third set of 3D protein structure models to accommodate molecular conformations; and generating, for the second protein anti-target, a fourth set of interaction sites comprising a fourth set of 3D protein structure models to accommodate molecular conformations;

derivatizing a plurality of candidate small molecule compounds (SMCs) from a SMC seed model;

generating, utilizing the digital protein receptor panel, SMC therapeutic interaction scores for each candidate SMC in the plurality of candidate SMCs by:

simulating, for a candidate SMC in the plurality of candidate SMCs, first target interactions between the candidate SMC and the first set of 3D protein structure models from the first set of interaction sites of the digital protein receptor panel corresponding to the first protein target to generate first target interaction scores by utilizing a machine learning model to predict binding affinities between the first set of 3D protein structure models from the first set of interaction sites of the digital protein receptor panel corresponding to the first protein target and utilizing a weight corresponding to an interaction site from the first set of interaction sites and an additional weight corresponding to an additional interaction site from the first set of interaction sites;

simulating, for the candidate SMC in the plurality of candidate SMCs, second target interactions between the candidate SMC and the second set of 3D protein structure models from the second set of interaction sites of the digital protein receptor panel corresponding to the second protein target to generate second target interaction scores;

simulating, for the candidate SMC in the plurality of candidate SMCs, first anti-target interactions between the candidate SMC and the third set of 3D protein structure models from the third set of interaction sites of the digital protein receptor panel corresponding to the first protein anti-target to generate first anti-target interaction scores;

simulating, for the candidate SMC in the plurality of candidate SMCs, second anti-target interactions between the candidate SMC and the fourth set of 3D protein structure models from the fourth set of interaction sites of the digital protein receptor panel corresponding to the second protein anti-target to generate second anti-target interaction scores; and generating a SMC therapeutic interaction score by combining the first target interaction scores, the second target interaction scores, the first anti-target interaction scores, and the second anti-target inter-
action scores, wherein the SMC therapeutic interac-
tion score comprises a singular score that indicates a
capability of the candidate SMC to interact with the
first protein target, the second protein target, the first
protein anti-target, and the second protein anti-target
corresponding to the pharmaceutical therapy;

determining a polypharmacological drug by selecting a
SMC from the plurality of candidate SMCs based on a
particular SMC therapeutic interaction score corre-
sponding to the SMC satisfying a SMC interaction
score threshold; and synthesizing the determined polypharmacological drug.

2. The method of claim 1, further comprising:

derivatizing a plurality of additional candidate SMCs
from the plurality of candidate SMCs;

generating, utilizing the digital protein receptor panel,
additional SMC therapeutic interaction scores for each
the additional candidate SMC in the plurality of addi-
tional candidate SMCs by:

simulating, for an additional candidate SMC in the
  plurality of additional candidate SMCs, first addi-
  tional target interactions between the additional can-
  didate SMC and the first set of 3D protein structure
  models from the first set of interaction sites of the
  digital protein receptor panel corresponding to the
  first protein target to generate first additional target
  interaction scores;

simulating, for the additional candidate SMC in the
  plurality of additional candidate SMCs, second addi-
  tional target interactions between the additional can-
  didate SMC and the second set of 3D protein struc-
  ture models from the second set of interaction sites
  of the digital protein receptor panel corresponding to
  the second protein target to generate second addi-
  tional target interaction scores;

simulating, for the additional candidate SMC in the
  plurality of additional candidate SMCs, first addi-
  tional anti-target interactions between the additional
  candidate SMC and the third set of 3D protein
  structure models from the third set of interaction
  sites of the digital protein receptor panel correspond-
  ing to the first protein anti-target to generate first
  additional anti-target interaction scores;

simulating, for the additional candidate SMC in the
  plurality of additional candidate SMCs, second addi-
  tional anti-target interactions between the additional
  candidate SMC and the fourth set of 3D protein
  structure models from the fourth set of interaction
  sites of the digital protein receptor panel correspond-
  ing to the second protein anti-target to generate
  second additional anti-target interaction scores; and generating an additional SMC therapeutic interaction
  score by combining the first additional target inter-
  action scores, the second additional target interaction
  scores, the first additional anti-target interaction
  scores, and the second additional anti-target interac-
  tion scores; and determining the polypharmacological drug by selecting
an additional SMC from the plurality of additional
candidate SMCs based on comparing the additional
SMC therapeutic interaction scores to the SMC inter-
action score threshold.

3. The method of claim 1, further comprising, prior to
simulating the first target interactions, updating the plurality
of candidate SMCs by removing a subset of candidate SMCs
based on screening criteria.

4. The method of claim 3, wherein the screening criteria
comprise at least one selected from a group consisting of
ADMET properties, synthesizability, and similarity to
known drugs.

5. The method of claim 1, wherein derivatizing the
plurality of candidate SMCs from the SMC seed model
comprises generating multiple molecule combinations from
the SMC seed model.

6. The method of claim 1, wherein generating the SMC
therapeutic interaction score comprises:

increasing the SMC therapeutic interaction score utilizing
the first target interaction scores and the second target
interaction scores; and decreasing the SMC therapeutic interaction score utilizing
the first anti-target interaction scores and the second
anti-target interaction scores.

7. The method of claim 1, further comprising simulating
target interactions between the candidate SMC and the first
protein target by utilizing the machine learning model with
a feature representation of the candidate SMC and a plurality
of feature representations for each of the first protein target
to generate binding affinity predictions between the candi-
date SMC and the first set of 3D protein structure models
from the first set of interaction sites of the digital protein
receptor panel corresponding to the first protein target.

8. The method of claim 1, further comprising:

utilizing the polypharmacological drug in a therapeutic
treatment to target one or more proteins.

9. A method for differential drug discovery, the method
comprising:

generating a digital protein receptor panel relating to a
pharmaceutical therapy of a first protein target, a sec-
ond protein target, a first protein anti-target, and a
second protein anti-target by:

generating, for the first protein target, a first set of
  interaction sites comprising a first set of three-
  dimensional (3D) protein structure models to accom-
  modate molecular conformations;

generating, for the second protein target, a second set of
  interaction sites comprising a second set of 3D
  protein structure models to accommodate molecular
  conformations;

generating, for the first protein anti-target, a third set of
  interaction sites comprising a third set of 3D protein
  structure models to accommodate molecular confor-
  mations; and generating, for the second protein anti-target, a fourth
  set of interaction sites comprising a fourth set of 3D
  protein structure models to accommodate molecular
  conformations;

generating, utilizing the digital protein receptor panel, a
SMC therapeutic interaction score for a candidate SMC
by:

simulating, for the candidate SMC, first target interac-
  tions between the candidate SMC and the first set of
  3D protein structure models from the first set of
  interaction sites of the digital protein receptor panel
  corresponding to the first protein target to generate
  first target interaction scores by utilizing a machine
  learning model to predict binding affinities between
  the first set of 3D protein structure models from the
  first set of interaction sites of the digital protein
  receptor panel corresponding to the first protein
  target and utilizing a weight corresponding to an
  interaction site from the first set of interaction sites and an additional weight corresponding to an additional interaction site from the first set of interaction sites;

simulating, for the candidate SMC, second target interactions between the candidate SMC and the second set of 3D protein structure models from the second set of interaction sites of the digital protein receptor panel corresponding to the second protein target to generate second target interaction scores;

simulating, for the candidate SMC, first anti-target interactions between the candidate SMC and the third set of 3D protein structure models from the third set of interaction sites of the digital protein receptor panel corresponding to the first protein anti-target to generate first anti-target interaction scores;

simulating, for the candidate SMC, second anti-target interactions between the candidate SMC and the fourth set of 3D protein structure models from the fourth set of interaction sites of the digital protein receptor panel corresponding to the second protein anti-target to generate second anti-target interaction scores; and generating the SMC therapeutic interaction score by combining the first target interaction scores, the second target interaction scores, the first anti-target interaction scores, and the second anti-target interaction scores, wherein the SMC therapeutic interaction score comprises a singular score that indicates a capability of the candidate SMC to interact with the first protein target, the second protein target, the first protein anti-target, and the second protein anti-target corresponding to the pharmaceutical therapy; and synthesizing a polypharmacological drug from the candidate SMC based on the SMC therapeutic interaction score corresponding to the candidate SMC satisfying a SMC interaction score threshold.

10. The method of claim 9, wherein the first set of interaction sites comprises multiple 3D protein structure models for the first protein target.

11. The method of claim 9, further comprising generating the SMC therapeutic interaction score by:

increasing the SMC therapeutic interaction score utilizing the first target interaction scores and the second target interaction scores; and decreasing the SMC therapeutic interaction score utilizing the first anti-target interaction scores and the second anti-target interaction scores.

12. The method of claim 9, further comprising simulating the first target interactions by utilizing a molecular docking between the first set of 3D protein structure models from the first set of interaction sites of the digital protein receptor panel corresponding to the first protein target.

13. The method of claim 9, further comprising generating additional SMC therapeutic interaction scores for each additional candidate SMCs in a plurality of additional candidate SMCs based on second additional target interactions and second additional anti-target interactions in the digital protein receptor panel.

14. The method of claim 9, further comprising derivatizing the candidate SMC from a SMC seed model.

15. A method for differential drug discovery, the method comprising:

generating a digital protein receptor panel relating to a pharmaceutical therapy of a first protein target, a second protein target, a first protein anti-target, and a second protein anti-target by:

generating, for the first protein target, a first set of interaction sites comprising a first set of three-dimensional (3D) protein structure models to accommodate molecular conformations;

generating, for the second protein target, a second set of interaction sites comprising a second set of 3D protein structure models to accommodate molecular conformations;

generating, for the first protein anti-target, a third set of interaction sites comprising a third set of 3D protein structure models to accommodate molecular conformations; and generating, for the second protein anti-target, a fourth set of interaction sites comprising a fourth set of 3D protein structure models to accommodate molecular conformations;

identifying a plurality of candidate small molecule compounds (SMCs);

generating, utilizing the digital protein receptor panel, SMC therapeutic interaction scores for each candidate SMC in the plurality of candidate SMCs by:

simulating, for a candidate SMC in the plurality of candidate SMCs, first target interactions between the candidate SMC and the first set of 3D protein structure models from the first set of interaction sites of the digital protein receptor panel corresponding to the first protein target to generate first target interaction scores by utilizing a machine learning model to predict binding affinities between the first set of 3D protein structure models from the first set of interaction sites of the digital protein receptor panel corresponding to the first protein target and utilizing a weight corresponding to an interaction site from the first set of interaction sites and an additional weight corresponding to an additional interaction site from the first set of interaction sites;

simulating, for the candidate SMC in the plurality of candidate SMCs, second target interactions between the candidate SMC and the second set of 3D protein structure models from the second set of interaction sites of the digital protein receptor panel corresponding to the second protein target to generate second target interaction scores;

simulating, for the candidate SMC in the plurality of candidate SMCs, first anti-target interactions between the candidate SMC and the third set of 3D protein structure models from the third set of interaction sites of the digital protein receptor panel corresponding to the first protein anti-target to generate first anti-target interactions scores;

simulating, for the candidate SMC in the plurality of candidate SMCs, second anti-target interactions between the candidate SMC and the fourth set of 3D protein structure models from the fourth set of interaction sites of the digital protein receptor panel corresponding to the second protein anti-target to generate second anti-target interaction scores; and generating a SMC therapeutic interaction score by combining the first target interaction scores, the second target interaction scores, the first anti-target interaction scores, and the second anti-target interaction scores, wherein the SMC therapeutic interaction score comprises a singular score that indicates a capability of the candidate SMC to interact with the first protein target, the second protein target, the first protein anti-target, and the second protein anti-target corresponding to the pharmaceutical therapy;

determining a polypharmacological drug by selecting a SMC from the plurality of candidate SMCs based on a particular SMC therapeutic interaction score corresponding to the SMC satisfying a SMC interaction score threshold; and synthesizing the determined polypharmacological drug.

16. The method of claim 15, further comprising:

derivatizing a plurality of additional candidate SMCs from the plurality of candidate SMCs;

generating, utilizing the digital protein receptor panel, additional SMC therapeutic interaction scores for each additional candidate SMC in the plurality of additional candidate SMCs by:

simulating, for an additional candidate SMC in the plurality of additional candidate SMCs, additional target interactions between the additional candidate SMC and the first set of interaction sites or the second set of interaction sites of the digital protein receptor panel corresponding to the first protein target or the second protein target to generate additional target interaction scores;

simulating, for the additional candidate SMC in the plurality of additional candidate SMCs, additional anti-target interactions between the additional candidate SMC and the third set of interaction sites or the fourth set of interaction sites of the digital protein receptor panel corresponding to the first protein anti-target or the second protein anti-target to generate additional anti-target interaction scores; and generating an additional SMC therapeutic interaction score by combining the additional target interaction scores and the additional anti-target interaction scores; and determining the polypharmacological drug by selecting an additional SMC from the plurality of additional candidate SMCs based on comparing the additional SMC therapeutic interaction scores to the SMC interaction score threshold.

17. The method of claim 15, further comprising updating the plurality of candidate SMCs by removing a subset of candidate SMCs based on screening criteria, wherein the screening criteria is determined utilizing ADMET properties of the plurality of candidate SMCs.

18. The method of claim 15, further comprising generating the SMC therapeutic interaction score by:

increasing the SMC therapeutic interaction score utilizing the first target interaction scores and the second target interaction scores; and decreasing the SMC therapeutic interaction score utilizing the first anti-target interaction scores and the second anti-target interaction scores.

19. The method of claim 15, wherein the first set of interaction sites comprises multiple 3D protein structure models for the first protein target and the third set of interaction sites comprises additional multiple 3D protein structure models for the first protein anti-target.

20. The method of claim 15, further comprising simulating the target interactions between the candidate SMC and the first protein target by utilizing the machine learning model with a feature representation of the candidate SMC and a plurality of feature representations for each of the first protein target to generate binding affinity predictions between the candidate SMC and the first set of 3D protein structure models from the first set of interaction sites of the digital protein receptor panel corresponding to the first protein target.

* * * * *